United States Patent
Xu et al.

(10) Patent No.: US 9,023,795 B2
(45) Date of Patent: May 5, 2015

(54) ANGIOGENESIS-INHIBITING PEPTIDE AND APPLICATION THEREOF

(75) Inventors: Xun Xu, Shanghai (CN); Ying Zheng, Shanghai (CN); Hui Zhao, Shanghai (CN)

(73) Assignee: Shanghai First People's Hospital, Shanghai (CN)

( * ) Notice: Subject to any disclaimer, the term of this patent is extended or adjusted under 35 U.S.C. 154(b) by 0 days.

(21) Appl. No.: 13/819,175

(22) PCT Filed: Jul. 1, 2011

(86) PCT No.: PCT/CN2011/076761
§ 371 (c)(1),
(2), (4) Date: Feb. 26, 2013

(87) PCT Pub. No.: WO2012/013111
PCT Pub. Date: Feb. 2, 2012

(65) Prior Publication Data
US 2013/0172258 A1    Jul. 4, 2013

(30) Foreign Application Priority Data
Jul. 26, 2010 (CN) .......................... 2010 1 0235580

(51) Int. Cl.
| | | |
|---|---|---|
| C07K 14/00 | (2006.01) | |
| C07K 7/08 | (2006.01) | |
| C07K 14/47 | (2006.01) | |
| C07K 14/475 | (2006.01) | |
| C07K 14/52 | (2006.01) | |
| A61K 38/18 | (2006.01) | |
| A61K 38/17 | (2006.01) | |
| A61K 38/00 | (2006.01) | |

(52) U.S. Cl.
CPC ................ C07K 14/00 (2013.01); *A61K 38/18* (2013.01); *A61K 38/1891* (2013.01); *A61K 38/179* (2013.01); *A61K 38/00* (2013.01); C07K 14/4715 (2013.01); C07K 14/4753 (2013.01); C07K 14/52 (2013.01); C07K 7/08 (2013.01)

(58) Field of Classification Search
CPC ... A61K 38/10; A61K 38/16; A61K 38/1866; A61K 38/00; A61K 38/179; A61K 38/18; A61K 38/1891; C07K 7/08; C07K 14/00; C07K 14/475; C07K 14/4715; C07K 14/4753; C07K 14/52
See application file for complete search history.

(56) References Cited

U.S. PATENT DOCUMENTS

2009/0068679 A1    3/2009    Vitzthum et al.

FOREIGN PATENT DOCUMENTS

| WO | WO 2008146023 A1 * | 12/2008 | ............. C07K 14/52 |
| WO | 2010/065995 | 6/2010 | |

OTHER PUBLICATIONS

Rudinger, Peptide Hormones, JA Parsons, Ed., 1976, pp. 1-7.*
SIGMA, 2004, pp. 1-2.*
Berendsen, A Glimpae of the Holy Grail?, Science, 1998, 282, pp. 642-643.*
Voet et al, Biochemistry, John Wiley & Sons Inc., 1995, pp. 235-241.*
Ngo et al, Computational Complexity, Protein Structure Protection, and the Levinthal Paradox, 1994, pp. 491-494.*
Bradley et al., Limits of Cooperativity in a Structurally Modular Protein: Response of the Notch Ankyrin Domain to Analogous Alanine Substitutions in Each Repeat, J. Mol. BloL (2002) 324, 373-386.*
Sequence Listing for Toivanen et al. (WO 2008146023 A1) as reference above, 2008.*
Black Flying Fox Placenta growth factor protein sequence, Accession No. L5JQM1 (L5JQM1_PTEAL), p. 2, accessed on Jun. 3, 2014.*
Pig Placenta growth factor protein sequence, Accession No. B6DXF1 (B6DXF1_PIG), p. 2, accessed on Jun. 3, 2014.*
Shakhashiri, www.scifun.org, Chemical of the Week, Water, Jan. 2011.*
Takeda, Treatment with Recombinant Placental Growth Factor Enhances Both Angiogenesis and Arteriogenesis and Improves Survival after Myocardial Infarction, Circ J. 2009; 73:1674-1682.*
Brian Annex, Growth Factor induced therapeutic angiogenesis in the heart: protein therapy, cardiovascular research, 65 (2005) 649-655.*
International Search Report from Application PCT/CN2011/076761, dated Sep. 15, 2011, 10 pages.
Eriksson et al., Placenta Growth Factor-1 antagonizes VEGF—induced angiogenesis and tumor growth by the formation of functionally inactive PIGF-1/VEGF heterodimers, Cancer Cell, Feb. 2002, pp. 99-108.
Domenico Ribatti, The discovery of the placental growth factor and its role in angiogenesis: a historical review, Springer Science+Business Media B.V. 2008, pp. 215-221.

* cited by examiner

*Primary Examiner* — James H Alstrum Acevedo
*Assistant Examiner* — Erinne Dabkowski
(74) *Attorney, Agent, or Firm* — Hamre, Schumann, Mueller & Larson, P.C.

(57) ABSTRACT

Provided is a polypeptide having angiogenesis inhibiting activity. The polypeptide is derived from Placenta Growth Factor-1. Also provided are a derivative polypeptide of the polypeptide, a preparation method for polypeptide, and a pharmaceutical composition containing the polypeptide.

7 Claims, 6 Drawing Sheets

ANGIOGENESIS-INHIBITING PEPTIDE AND APPLICATION THEREOF

TECHNICAL FIELD

The present invention relates to bio-pharmaceutical field. In particular, the present invention relates to a novel polypeptide inhibiting angiogenesis, and said polypeptide is derived from Placenta Growth Factor (PLGF). The present invention further relates to a method for preparing the polypeptide, use thereof, and a pharmaceutical composition comprising the polypeptide.

TECHNICAL BACKGROUND

Angiogenesis involves extremely complicated courses including expansion of existing vessels, increasing of vascular permeability, degradation of perivascular stroma, activation, proliferation and migration of endothelial cells, and formation of new capillary-like lumina.

About ⅔ of diseases causing blindness are associated with pathological angiogenesis in eyes. For example, corneal angiogenesis induced with simplex herpetic stromal keratitis, choroidal angiogenesis in age-related macular degeneration, and retinal angiogenesis in diabetic retinopathy or retinopathy of premature infant. Clinically in present, laser photocoagulation, photodynamic therapy (PDT), and thermal transpupillary therapy (TTT) etc. are conventionally used for treating the ocular pathological angiogenesis. However, these treatments tend to easily destroy local tissues, and the long-term efficacy thereof is still unsatisfactory. Therefore, in recent years, people kept trying to develop more effective methods for treating ocular pathological angiogenesis.

When developing effective inhibitors of angiogenesis, the specificity of the ocular drugs should be sufficiently considered.

Firstly, there are many anatomical and functional barriers in eyes. Systemic administration usually cannot result in a topically sufficient drug concentration in ocular tissue due to the blood-aqueous humor barrier and blood-retina barrier. Theoretically, in topical administration, such as injection in vitreous cavity, it is difficult for any macromolecule larger than 76.5 kDa to penetrate the retina to act on the retinal and choroidal angiogenesis. When administrated on ocular surface, the drugs have to successively penetrate lipophilic the corneal epithelial cells as well as the hydrophilic corneal stroma, which are tightly connected. Thus, merely the medications that have appropriate lipophilicity, a low molecular weight or capability to bind with the transporters (e.g., amino acid transporters, oligopeptide transporters, etc.) in ocular surface tissues can reach the anterior chamber and function effectively.

Secondly, the solubility of the drugs in the hydrophilic tears, aqueous humor, and vitreous humor is positively correlated to their effects.

Thirdly, for the above major reasons, the bioavailability of ocular drugs is very low. To improve it, the concentration of drugs administered may be increased. However, compounds for treating neoplastic angiogenesis exhibit obvious toxicity, so that high dose cannot be used in either systemic or topical administration. In addition, exogenous proteins with large molecular weight are also foreign substances for allergy which may cause immune damages to eye tissues such as uveal.

Fourthly, currently a series of relatively safe endogenous inhibitors of angiogenesis, such as angiostatin consisting of plasminogen Kringle domains 1-4, have been demonstrated to obviously inhibit growth of vessel blood-dependent tumor. However, due to their relative large molecular weight and complicated spatial conformation, these inhibitors have disadvantages such as complicated recombinant expression and purification processes in preparation, residual endotoxin and so on.

Because of the constraints caused by the above factors, there are only few medications at present for treating ocular angiogenesis, e.g., recombinant anti-VEGF monoclonal antibody bevacizumab (AVASTIN®), and the recombinant fragment of anti-human VEGF monoclonal antibodies ranibizumab (LUCENTIS®), etc. However, they are expensive and it is necessary to repeat intravitreal administrations which even cause a risk of vascular embolization, etc.

Therefore, there is an urgent need in developing inhibitors of angiogenesis, which are small molecules, safe and effective, and compatible with eyeball tissues.

SUMMARY OF INVENTION

The purpose of the present invention is to provide a small molecular polypeptide, and the fragments, analogs, and derivatives thereof, which are compatible with eyeball tissue, effective and safe for inhibit angiogenesis.

The other purpose of the present invention is to provide a method for preparing said polypeptide and use of said polypeptide.

In the first aspect, the present invention provides a polypeptide represented by the following formula I, or a pharmaceutically acceptable salt thereof,

[Xaa0]-[Xaa1]-[Xaa2]-[Xaa3]-[Xaa4]-[Xaa5]-[Xaa6]-[Xaa7]-[Xaa8]-[Xaa9]-[Xaa10]-[Xaa11]-[Xaa12]-[Xaa13]-[Xaa14]-[Xaa15]-[Xaa16]-[Xaa17]-[Xaa18]   (I)

wherein,

Xaa0 is none, or a peptide segment consisting of 1-3 amino acids;
Xaa1 is selected from the group consisting of Val or Leu;
Xaa2 is selected from the group consisting of Ser or Thr;
Xaa3 is selected from the group consisting of Leu, Ile, Val, or Ala;
Xaa4 is selected from the group consisting of Leu, Ile, Val, or Ala;
Xaa5 is selected from the group consisting of Arg or Lys;
Xaa6 is selected from the group consisting of Cys or Ser;
Xaa7 is selected from the group consisting of Thr or Ser;
Xaa8 is selected from the group consisting of Gly or Ala;
Xaa9 is selected from the group consisting of Cys or Ser;
Xaa10 is selected from the group consisting of Cys or Ser;
Xaa11 is selected from the group consisting of Gly or Ala;
Xaa12 is selected from the group consisting of Asp or Glu;
Xaa13 is selected from the group consisting of Glu or Asp;
Xaa14 is selected from the group consisting of Asn or Gln;
Xaa15 is selected from the group consisting of Leu, Ile, Val, or Ala;
Xaa16 is selected from the group consisting of His or Arg;
Xaa17 is selected from the group consisting of Cys or Ser;
Xaa18 is none, or a peptide segment consisting of 1-3 amino acids;
and the polypeptide exhibits an activity of inhibiting angiogenesis and has a length of 17-23 amino acids.

In another preferred embodiment, Xaa18 is a segment consisting of 3 amino acids. More preferably, said segment is VPV, APA, APV, VPA or VSL.

In another preferred embodiment, Xaa0 is Cys.

In another preferred embodiment, the length of the polypeptide is 18-21 amino acids.

In another preferred embodiment, the polypeptide is selected from the group consisting of:

(a) a polypeptide having the amino acid sequence represented by SEQ ID NO:1, 2 3 or 4;

(b) a polypeptide which is derived from the polypeptide of (a) by substitution, deletion, or addition of 1-5 amino acids (preferably 1-3, and more preferably 1-2) in the amino acid sequence of SEQ ID NO: 1, 2, 3 or 4 and which has the activity of inhibiting angiogenesis.

In another preferred embodiment, said derived polypeptide retains 70% activity to inhibit angiogenesis of polypeptide represented by SEQ ID NO.: 1.

In another preferred embodiment, the homology between said derived polypeptide and the sequence of SEQ ID No.: 1 is ≥80%, preferably ≥90%; and more preferably ≥95%.

The present invention further provides a dimer form and a polymer form of the compound of formula I, which exhibit the activity of inhibiting angiogenesis.

In the second aspect, the present invention provides an isolated nucleic acid molecule encoding the above-mentioned polypeptide of the present invention.

In the third aspect, the present invention provides a pharmaceutical composition comprising:

(a) the above-mentioned polypeptide or a pharmaceutically acceptable salt thereof of the present invention; and (b) a pharmaceutically acceptable carrier or excipient.

In another preferred embodiment, the dosage form of the composition is eyedrop, injection solution (such as injection solution for using around or inside the eye), and ophthalmic gel or eye ointment.

In another preferred embodiment, the composition is in a slow release dosage form.

In the fourth aspect, the present invention provides a use of said polypeptide or a pharmaceutically acceptable salt thereof for preparing a medicament for inhibiting angiogenesis, or preventing or treating diseases associated with angiogenesis.

In another preferred embodiment, the disease associated with angiogenesis is selected from the group consisting of neovascular eye diseases, tumor, ischemic heart disease, non-inflammatory myocardiopathy, coronary sclerosis, arteriosclerosis obliterans, artery embolism, artery thrombus, Berger's disease, chronic inflammation, inflammatory intestinal diseases, ulcer, rheumatic arthritis, scleroderma, psoriasis, infertility and sarcoma-like diseases.

In another preferred embodiment, the neovascular eye diseases include diseases involved in choroid, retina, cornea or iris, including age-related macular degeneration, proliferative diabetic retinopathy, retinal vessel-blocked diseases, retinopathy of prematurity, corneal infection, and neovascular glaucoma.

In the fifth aspect, the present invention provides a method for inhibiting angiogenesis in mammal, comprising the step of administering the polypeptide or a pharmaceutically acceptable salt thereof of the present invention to a subject in need thereof.

In another preferred embodiment, the subject is a human.

In another preferred embodiment, the angiogenesis is associated with neovascular eye diseases.

DESCRIPTION OF DRAWINGS

The following descriptions of drawings are to illustrate the specific embodiments of the present invention. They should not be construed as limiting the scope of the present invention, which should be defined by the claims.

DETAILED DESCRIPTION OF THE INVENTION

Figure 1:
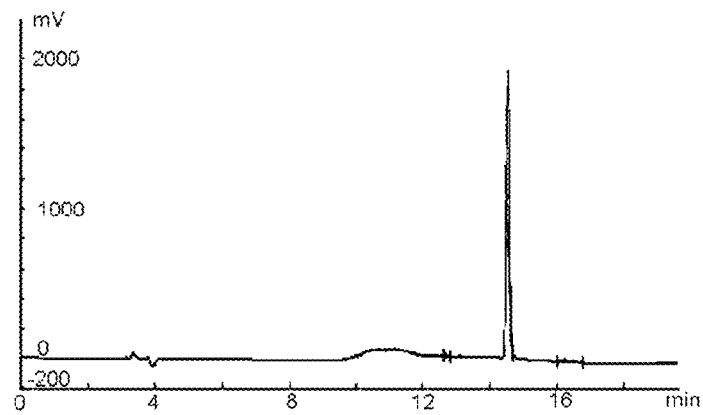
FIG. 1 shows the purity identification of the ZY1 small peptide with High Performance Liquid Chromatography (HPLC) Analysis.

After extensive and intensive studies, the inventors have firstly prepared a class of small molecular polypeptides which are derived from Placental Growth Factor, exhibit a function of inhibiting angiogenesis and have a molecular weight of less than 5 kD (for example, just about 3 KD). In particular, by utilizing the method of bioinformatics, the inventor designed several candidate sequences based on the homology analysis and analysis on the biological properties. After synthesizing these sequences via solid phase synthesis and further screening them through the model of vessels on chick embryo chorioallantoic membrane, the model of the corneal angiogenesis mouse induced with VEGF, and the model of retinal angiogenesis mouse induced with hypoxia, the inventors obtained a class of novel, small molecular polypeptides exhibiting the function of preventing and treating angiogenesis.

The small peptides of the present invention have a small molecular weight. They can penetrate through various ocular tissue barriers. They have good water solubility, so that they can maintain a relatively high concentration in neutral tears, aqueous humor and vitreous humor. They are highly safe with a minor toxicity or side-effect to the biological tissue. The bioavailability in eye topical administration is high, thus the dose can be reduced, and hence the systemic toxicity can also be reduced. Based on the above work, the inventors finish the present invention.

Active Polypeptides

In the present invention, the terms "the polypeptide(s) of the present invention", "ZY polypeptide(s)", "ZY small peptide(s)", "short peptide(s) ZY" and "peptide(s) ZY" are interchangeable and refer to the protein or polypeptide having peptide ZY amino acid sequence (SEQ ID NO: 1-4) and exhibiting an activity of inhibiting angiogenesis. In addition, said terms comprise the variants of SEQ ID NO: 1-4 which exhibit the function of inhibiting angiogenesis. These variations include, but are not limited to, deletions, insertions and/or substitutions of 1-5 (typically 1-4, preferably 1-3, more preferably 1-2, most preferably 1) amino acids, and addition of one or more (typically less than 5, preferably less than 3, more preferably less than 2) amino acids at C-terminus and/or N-terminus. For example, the protein's functions are usually unchanged when an amino residue is substituted by a similar or analogous one in the art. Further, the addition of one or several amino acids at C-terminus and/or N-terminus generally will not change the structure and function of protein. Furthermore, the terms also include the monomer and polymer of the polypeptide of the present invention. The terms also include the linear and nonlinear polypeptides (such as cyclic peptides).

The present invention further includes the active fragments, derivatives and analogs of ZY polypeptide. As used herein, the terms "fragments", "derivatives" and "analogs" refer to the polypeptides basically maintaining the function or activity of inhibiting angiogenesis. The polypeptide fragments, derivatives or analogs of the present invention may be (i) a polypeptide with one or more conservative or non-conservative amino acid residues (preferably the conservative amino acid residues) being substituted, or (ii) a polypeptide having substituted group(s) in one or more amino acid residues, or (iii) a polypeptide formed by fusion of ZY polypeptide with another compound (such as the compound that prolongs the half life of the polypeptide, such as polyethylene glycol), or (iv) a polypeptide with additional amino acid sequence fused to said polypeptide sequence, such as fusion proteins formed by fusion with leader sequence, secretion sequence or tag sequence, such as 6H is. According to the subject application, these fragments, derivatives and analogs are within the scope commonly known by the skilled person.

A class of preferred active derivatives is the polypeptides formed by replacing at most 5, preferably at most 3, more preferably at most 2, most preferably 1 amino acid of the amino acid sequence represented by formula I with the amino acid having similar or analogous property. These conservative variant polypeptides are preferably formed by carrying out the amino acid replacement according to Table I. A preferred polypeptide derivative is showed in SEQ ID NO: 3.

TABLE I

| Initial residue | Representative substitution | Preferred substitution |
|---|---|---|
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

The present invention also provides the analogues of ZY polypeptide. These analogues can differ from naturally occurring ZY polypeptide by amino acid sequence differences or by modifications that do not affect the sequence, or by both. Also included are analogues which include residues other than those naturally occurring L-amino acids (e.g., D-amino acids) or non-naturally occurring or synthetic amino acids (e.g., beta- or gamma-amino acids). It is understood that the polypeptides of the present invention are not limited to the representative polypeptides listed hereinabove.

Modifications (which do not normally alter the primary sequence) include in vivo or in vitro chemical derivation of polypeptides, e.g., acetylation, or carboxylation. Also included is modification of glycosylation, e.g., the polypeptides made by subjecting to the glycosylation modification during its synthesis and processing or in the further processing steps. These modifications can be accompanied by exposing the polypeptide to enzymes which affect glycosylation (e.g., mammalian glycosylating or deglycosylating enzymes). Also included are sequences that have phosphorylated amino acid residues, e.g., phosphotyrosine, phosphoserine, phosphothronine, as well as sequences that have been modified to improve their resistance to proteolytic degradation or to optimize solubility properties.

The polypeptides of the present invention can be used in a form of pharmaceutically or physiologically acceptable salt derived from acid or base. Such salts include, but are not limited to, the salts formed with the following acids: hydrochloric acid, hydrobromic acid, sulfuric acid, citric acid, tartaric acid, phosphoric acid, lactic acid, pyruvic acid, acetic acid, succinic acid, oxalic acid, fumaric acid, maleic acid, oxaloacetic acid, methanesulfonic acid, ethyl-sulfonic acid, benzene sulfonic acid, or isethionic acid. Other salts include salts formed with alkali metals or alkaline earth metals (such as sodium, potassium, calcium or magnesium), and esters, carbamate or other conventional "prodrug" forms.

Encoding Sequences

The present invention further relates to a polynucleotide encoding ZY polypeptide. A preferred encoding sequence which encodes ZY1 short peptide as shown in SEQ ID NO: 1 is (SEQ ID NO: 5)
TGTGTCTCCCTGCTGCGCTGCACCGGCTGCTGCGGCGATGAGAATCTGC

ACTGTGTGCCGGTG.

The polynucleotide of the present invention can be in a form of DNA or RNA. DNA can be the coding strand or the non-coding strand. The coding sequence encoding the mature polypeptide can be identical to the coding sequence indicated in SEQ ID NO: 5, or can be a degenerate variant thereof. As used herein and taking SEQ ID NO.: 1 as an example, "degenerate variant" refers to a nucleic acid sequence which encodes the protein having the amino acid sequence of SEQ ID NO:1, but is different from the corresponding coding sequence in SEQ ID NO: 5.

The full length of ZY nucleotide sequence or fragment thereof of the present invention can be obtained via PCR amplification, recombinant method or artificial synthesis. Currently, the DNA sequence encoding the polypeptide (or fragment or derivative thereof) of the present invention can be prepared completely via chemical synthesis. Then the DNA sequence can be introduced into various existing DNA molecules (or such as vector) and cells known in the art.

The present invention also includes a vector containing the polynucleotide of the present invention, and a host cell engineered by the vector or the coding sequence of the ZY polypeptide of the present invention.

In another aspect, the present invention further comprises polyclonal antibodies or monoclonal antibodies to ZY peptide, especially the monoclonal antibodies.

Preparation Method

The polypeptide of the present invention can be a recombinant or synthetic polypeptide. The polypeptide of the present invention can be a chemically synthesized or recombinant polypeptide. Accordingly, the polypeptide of the present invention can be artificially synthesized via a conventional method, or can be produced via a recombinant method.

One preferred method is to use liquid phase synthesis technique or solid phase synthesis technique, such as Boc solid phase process, Fmoc solid phase process, or combination thereof. By using the solid phase synthesis, a sample can rapidly be obtained, and one can select a suitable resin carrier and synthesis system according to the sequence feature of the target peptide. For example, the preferred solid phase carrier in Fmoc system can be, such as Wang resin linked to the C-terminal amino acid of the peptide, wherein the structure of the Wang resin is polystyrene, the arm between the resin and the amino acid is 4-alkoxy benzyl alcohol. The Wang resin is treated with 25% hexahydropyridine/dimethylfomamide for 20 minutes under room temperature to remove the Fmoc protective groups. Then the sequence is extended from the C-terminus to the N-terminus according to the predetermined amino acid sequence. After synthesis, trifluoroacetic acid containing 4% p-methylphenol is used to cleave the peptide from the resin and the protective groups are removed. The resin can be filtered, and the crude peptide can be obtained via precipitation with ether. The solution of the resultant product is freeze-dried, gel-filtered, and purified by reverse phase HPLC to obtain the desired peptide. When utilizing the Boc system to perform the solid phase synthesis, preferably the resin is the PAM resin linked to the C-terminal amino acid of the peptide. The structure of the PAM resin is polystyrene, and the arm between the resin and the amino acid is 4-hydroxylmethyl phenylacetamide. In the Boc synthesis system, in the circle of deprotection, neutralization, and coupling, TFA/dichloromethane (DCM) is used to remove the protective group Boc, and diisopropylethylamine (DIEA)/dichloromethane is used for neutralization. After completion of peptide chain condensation, hydrogen fluoride (HF) containing p-methylphenol (5-10%) is used to treat the resin for 1 hour at 0° C., then the peptide chain is cleaved from the resin and the protective groups are removed at the same time. 50-80% acetic acid (containing a small amount of mercaptoethanol) is used to extract the peptide. The solution is freeze-dried, and then further isolated and purified by molecular screen Sephadex G10 or Tsk-40f. Then the desired peptide is obtained via high pressure liquid purification. Various coupling agents and coupling methods known in the peptide chemistry can be used to couple each amino acid residue. For example, dicyclohexylcarbodiimide (DCC), hydroxylbenzotriazole (HOBt) or 1,1,3,3-tetramethyluronium Hexafluorophosphate (HBTU) can be used for direct coupling. The purity and structure of the resultant short peptide can be verified by reverse phase HPLC and mass spectrometry.

In a preferred embodiment, the polypeptide ZY of the present invention is prepared by solid phase method according to its sequence, purified by high performance liquid chromatography, thereby obtaining freeze-dried powder of target peptide with high purity. The powder is stored at −20° C.

Another method is to produce the polypeptide of the present invention by a recombinant technique. With the conventional recombinant DNA technique, the polynucleotide of the present invention can be used to express or produce recombinant ZY polypeptides. Generally, the method comprises the following steps:

(1) Transforming or transfecting a suitable host cell with a polynucleotide or variant thereof encoding the ZY polypeptide of the present invention or a recombinant expression vector containing said polynucleotide;

(2) Culturing the host cell in a suitable culture medium;

(3) Isolating and purifying protein from the culture medium or cell.

The recombinant polypeptide may be included in the cells, or expressed on the cell membrane, or secreted out of the cell. If desired, the physical, chemical and other properties can be utilized in various isolation methods to isolate and purify the recombinant protein. These methods are well-known to those skilled in the art and include, but are not limited to, conventional renaturation treatment, treatment by protein precipitant (such as salt precipitation), centrifugation, cell lysis by osmosis, sonication, supercentrifugation, molecular sieve chromatography (gel chromatography), adsorption chromatography, ion exchange chromatography, high performance liquid chromatography (HPLC), and any other liquid chromatography, and the combination thereof.

It is also contemplated to link multiple polypeptides of the present invention in series due to their short length. After recombinant expression, the expression product is obtained in a form of polymer. Then the polymer is enzymatically cleaved to form the desired small peptides.

Pharmaceutical Composition and Methods of Administration

In another aspect, the present invention further provides a pharmaceutical composition, comprising (a) a safe and effective amount of the polypeptide of the present invention or a pharmaceutically acceptable salt thereof, and (b) a pharmaceutically acceptable carrier or excipient. The amount of the polypeptide of the present invention generally is 10 μg to 100 mg per dose, preferably 100-1000 μg per dose.

For the purpose of the invention, the effective dose is to administer to an individual about 0.01 mg to 50 mg of the polypeptide of the present invention per kg body weight, preferably 0.05 mg to 10 mg of the polypeptide of the present invention per kg body weight. Further, the polypeptide of the present invention can be used alone, or in combination with the other therapeutic agents (for example, formulated into the same pharmaceutical composition).

The pharmaceutical composition can further comprise a pharmaceutically acceptable carrier. The term "pharmaceutically acceptable carrier" refers to the carrier for using in administering the therapeutic agents. The term refers to such medical carriers that they themselves do not induce antibody deleterious to the subject having been administered the composition, and they do not have excessive toxicity after administration. These carriers are well known by the skilled person in the art. The detailed discussion about the pharmaceutically acceptable excipient can be found in Remington's Pharmaceutical Sciences (Mack Pub. Co., N.J., 1991). Such carriers include, but are not limited to, saline, buffer solution, glucose, water, glycerin, ethanol, adjuvant or the combination thereof.

The pharmaceutically acceptable carrier in the therapeutic composition can comprise solution, such as water, saline, glycerin, and ethanol. Further, these carriers can contain auxiliary substance(s), such as wetting agent or emulsifying agent, pH buffering substance, etc.

Typically, the therapeutic composition can be formulated into an injectable formulation, such as a liquid solution or suspension; or it may be in a solid form that is suitable to be formulated into a solution or suspension or liquid carrier before injection.

Once formulating the composition of the present invention, it can be administered via conventional routes which include, but are not limited to, administering on ocular surface, around the eye, intra-ocularly, intramuscularly, intravenously, subcutaneously, intracutaneously or topically. The subject to be prevented or treated may be an animal, especially a human.

When the pharmaceutical composition of the present invention is used in the actual treatment, the dosage form of the pharmaceutical composition can be varied according to the uses. Preferably, as an example, the dosage form may include eyedrop, injection, ophthalmic gel, and eye ointment.

The pharmaceutical composition can be formulated by mixing, diluting or dissolving according to the conventional methods. And, occasionally, suitable medical additives, such as excipients, disintegrating agents, adhesives, lubricants, diluting agents, buffering agents, isotonicities, preservatives, wetting agents, emulsifying agents, dispersing agents, stabilizing agents, and solubility promoters, may be added. Formulating can be carried out in a conventional manner according to the dosage form.

For example, formulation of eyedrop can be prepared as follows: dissolving short peptide ZY or a pharmaceutically acceptable salt thereof and the basic substances in sterile water (surfactant is dissolved in said water), adjusting osmotic pressure and alkalinity acidity to the physiological level, optionally adding suitable medical additives, such as preservatives, stabilizing agents, buffering agents, isotonicities, anti-oxidants and tackifiers, and then allowing them completely dissolved.

The pharmaceutical composition of the present invention can further be administered in a form of slow release formulation. For example, the short peptide ZY or salt thereof can be incorporated into the pill or microcapsule in which a slow release polymer is used as carrier, and then the pill or microcapsule is implanted into the tissue to be treated by operation. Furthermore, the short peptide ZY or salt thereof can be used by insertion of intra-ocular lens pre-coated with said drugs. Examples of the slow release polymer include ethylene-ethylene acetate copolymer, polyhydroxymethylacrylate, polyacrylamide, polyvinylpyrrolidone, methyl cellulose, polymer of lactic acid, lactic acid-glycolic acid copolymer, etc. Preferable examples of the slow release polymer include the biodegradable polymers, such as polymer of lactic acid, and lactic acid-glycolic acid copolymer.

When the pharmaceutical composition of the present invention is used in the actual treatment, the dose of the short peptide ZY or a pharmaceutically acceptable salt thereof, as an active ingredient, can be suitably determined according to the body weight, age, sex, symptom of each patient. For example, when topically dropping in the eye, the concentration of the active ingredient generally is 0.1-10 wt %, preferably 1-5 wt %, and administration is 2-6 times per day and 1-2 drops each time.

INDUSTRIAL APPLICABILITY

The pharmaceutical composition containing the peptide of the present invention or a pharmaceutically acceptable salt thereof as an active ingredient exhibits significant inhibition activity on angiogenesis. As verified by animal tests, the polypeptide of the present invention not only can inhibit angiogenesis in chick embryo chorioallantoic membrane, but also can inhibit the proliferation, migration, chemotaxis and lumen formation of HUVEC and the retinal angiogenesis in the hypoxia-induced mice.

The main advantages of the present invention include:

(a) The polypeptide of the present invention has small molecular weight, so it can penetrate ocular tissue barrier.

(b) The polypeptide of the present invention has good water solubility, so it can maintain relatively high concentration in neutral tears, aqueous humor and vitreous humor.

(c) The polypeptide of the present invention has high safety with less toxicity to the tissue of the organism. The bioavailability in eye topical administration is high, thus the dose can be reduced, and the systemic toxicity can also be reduced.

(d) The polypeptide of the present invention can be synthesized via solid phase synthesis with high purity, high yield and low cost.

(e) The polypeptide of the present invention is highly stable.

Therefore, the polypeptide of the present invention can be developed into a medicine for treating neovascular eye diseases and related diseases associated with angiogenesis, such as tumor angiogenesis, etc.

The invention is further illustrated by the following examples. These examples are only intended to illustrate the invention, but not to limit the scope of the invention. For the experimental methods in the following examples the specific conditions of which are not specifically indicated, they are performed under routine conditions, e.g., those described by Sambrook. et al., in Molecule Clone: A Laboratory Manual, New York: Cold Spring Harbor Laboratory Press, 1989, or as instructed by the manufacturers, unless otherwise specified.

Example 1

Synthesis of Polypeptide

The four ZY polypeptides represented by SEQ ID NO: 1-4 were synthesized by using the commercially available SYMPHONY polypeptide synthesizer.

```
                                        (SEQ ID NO: 1)
ZY1: CVSLLRCTGCC GDENLHCVPV (SEQ ID NO: 2)
ZY2: VSLLRCTGCCGDENLHCVPV;

(SEQ ID NO: 3)
ZY3: CVSLLRCTGCCGDENLHC;

(SEQ ID NO: 4)
ZY4: CASLLRCTGCCGDENLHCAPA
```

The steps were as follows: SYMIPHONY 12-channel peptide synthesizer (U.S. Protein Technologies. LLC.) was used and the reagents were calculated according to its software (Version. 201) and prepared. 2-Chlorotrityl Chloride Resin (Nankai Synthetic Technology Co., Ltd, Tianjin, China) was added into the reaction tubes and DMF (15 ml/g) (Dikma) was added and oscillation was carried out for 30 min. Solvents were suction filtered out through the sintered filter. 3-fold excess mole of Fmoc-L-Val-OH (small peptide ZY1), Fmoc-L-Val-OH (small peptide ZY2), Fmoc-L-Cys-OH (small the peptide ZY3) or Fmoc-L-Ala-OH (small peptide ZY4) amino acids (Suzhou Tianma Pharma Group Specialty Chemicals Co., Ltd.) were added and then 10-fold excess mole of DIEA (Sinopharm Shanghai Chemical Reagent Company) was added and finally DMF was added for dissolution. The mixture was oscillated for 30 min. DMF was removed and 20% piperidine (Sinopharm Shanghai Chemical Reagent Company) solution in DMF (15 ml/g) was added to react for 5 min. DMF was removed and another 20% piperidine solution in DMF (15 ml/g) was added to react for 15 min. Piperidine solution was suction filtered. A dozen tablets of resin were taken out and washed three times with ethanol. A droplet of ninhydrin solution, a droplet of KCN solution, and a droplet of phenol solution were added. Then, the mixture was heated to 105° C.-110° C. for 5 min and if color changed into dark blue, it indicated the positive reaction. The resins were washed with DMF (10 ml/g, twice), methanol (10 ml/g, twice), and DMF (10 ml/g, twice). 3-fold excess of both protected amino acids (FOMC-Asp-OH) and HBTU (Suzhou Tianma Pharma Group Specialty Chemicals Co., Ltd.) were added respectively. They were dissolved with little DMF and added into the reaction tube. Then 10-fold excess of NMM was immediately added and mixture was reacted for 30 min. It was washed with DMF (10 ml/g) once, methanol (10 ml/g) twice, and DMF (10 ml/g) twice. The above steps were repeated and the amino acids were connected from right to left according to the sequence of small peptides ZY1-4. After the connection of the last amino acid, the deprotection was carried out and the resins were washed with DMF (10 ml/g, twice), methanol (10 ml/g, twice), DMF (10 ml/g, twice) and DCM (10 ml/g, twice) respectively. Then the resins were drained for 10 min. The polypeptides were cleaved from the resins (cleavage fluid (10/g): 94.5% TFA (J. T. Baker), 2.5% water, 2.5% EDT (AILDRICH), 1% TIS (AILDRICH); cleavage time: 120 min). Protein lysate was sufficiently dried with nitrogen (Shanghai Biou Gas Industry Ltd.), washed six times with ether (Shanghai Shiyi Chemical Reagents Ltd.), and then dried at room temperature. Polypeptides were purified with HPLC (Models of SHIMADZU HPLC device: preparation model analytical model. Software: Class-VP, Sevial System, manufacturer: Shimadzu). The crude peptides were dissolved with pure water or small amount of acetonitrile (Fisher) and the eluted solution of small peptides ZY1-4 were respectively obtained by gradient elution. Finally, the purified solution was lyophilized to obtain small peptides ZY1-4 (120 mg for each, as white powder having good water solubility) with high purity (>95%). The peptides were sealed and stored at −20° C. before use.

Example 2

Identification and Storage of Small Peptides ZY1-4

A small amount of individual small peptides ZY1-4 was taken and a purity identification with HPLC analysis and a molecular weight identification with ESI-MS were conducted.

The results showed that:

the elution peak of ZY1 was at 14.532 minutes with the purity of 98.85% (FIG. 1);

the elution peak of ZY2 was at 7.944 minutes with the purity of 98.01%;

the elution peak of ZY3 was at 6.646 minutes with the purity of 98.63%;

the elution peak of ZY4 was at 10.045 minutes with the purity of 97.31%.

Small peptides ZY1 totally had 21 amino acids and 5 of which were Cys. MW: 2221.66;

Small peptides ZY2 totally had 20 amino acids and 4 of which were Cys. MW: 2118.52;

Small peptides ZY3 totally had 18 amino acids and 5 of which were Cys. MW: 1926.28;

Small peptides ZY4 totally had 21 amino acids and 5 of which were Cys. MW: 2137.50;

The small peptides in white powder form were sealed, packaged, and stored at −20° C.

Example 3

Inhibition Effect of Small Peptides ZY1-4 on Angiogenesis in Chick Embryo Chorioallantoic Membrane Model of chick embryo chorioallantoic membrane was used and the methods were as follows:

The chick fertile eggs of 1-2 days (purchased from 36 Lianhuaqing Chicken Farm of Shanghai Xinghuo Farm) were put into a thermhygrostat (T=37° C., Humidity H=60-70%) to incubate for 5 days after sterilization. The eggs were over-turned every morning and night. Onto the filter paper containing cortisone acetate (5 μg/μl, 5 μl/tablet), PBS (5 μl/tablet), low (2 µg/µl) or high (10 µg/µl) concentration of small peptides ZY1, ZY2, ZY3 or ZY4 (5 µl/tablet) were dropped respectively. After air-dried, the filter paper was placed between the major vessels on chorioallantoic membrane of fertile eggs and the eggs were sealed. The eggs were continuously placed in the thermhygrostat (T=37° C., Humidity H=60-70%) to incubate for 2 days without overturning. Then the chorioallantoic membrane was thoroughly exposed and photographed (the range was within 5 mm around the filter paper). The number of 3-5 subordinate microvessels in the area within 2.5 mm around the filter paper was counted. SPSS11.0.1 was used for statistical analysis.

Figure 2:
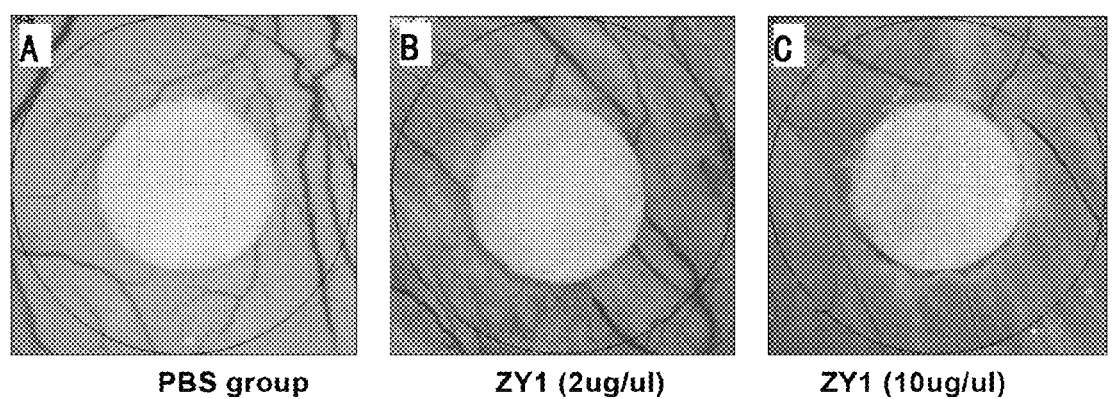
FIG. 2 shows the effect of ZY1 small peptide on angiogenesis in chick embryo chorioallantoic membrane. Panel A: the PBS group (negative control group). Panel B: low concentration (2 μg/μl) group of ZY1 small peptide. Panel C: high concentration (10 μg/μl) group of ZY1 small peptide. In Panel D, the vertical coordinate shows the amount of 3-5 subordinate microvessels in the area within 2.5 mm around the filter paper.
Figure 2:
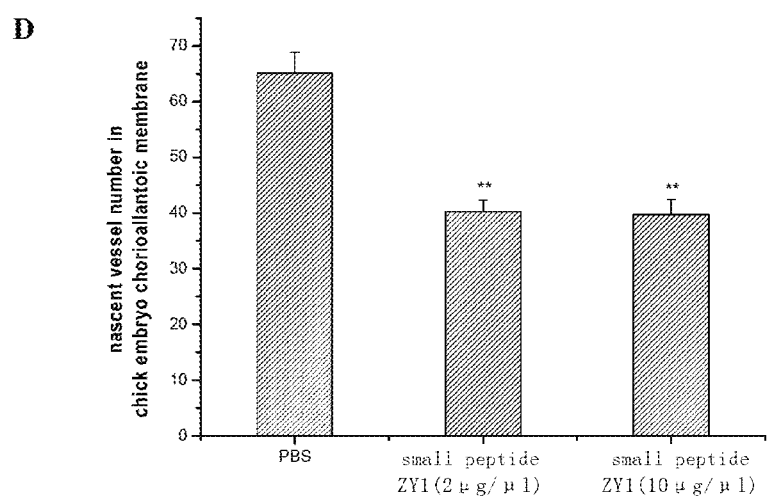
Figure 3:
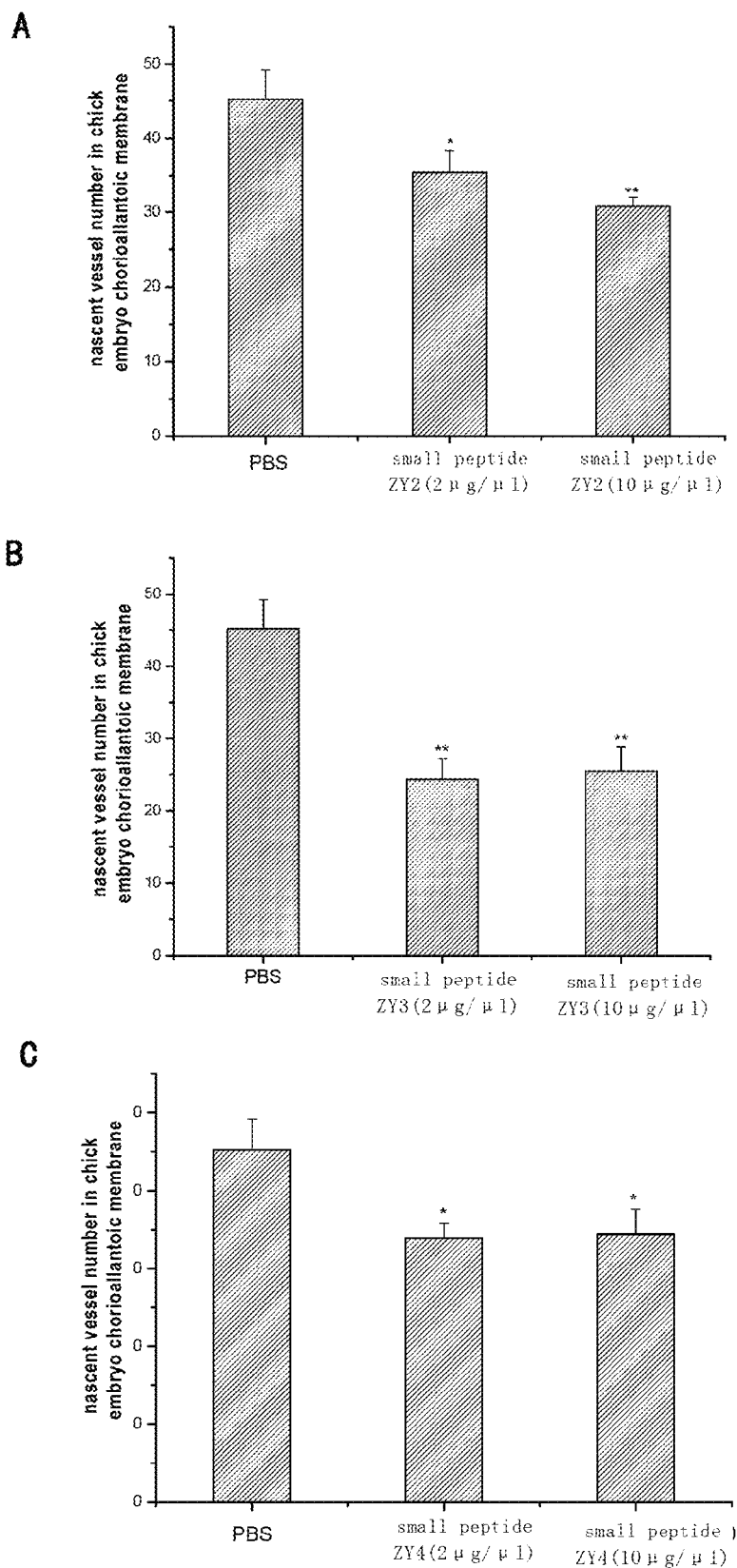
FIG. 3A to 3C show respectively the inhibition of ZY2-4 peptides on angiogenesis in chick embryo chorioallantoic membrane. Wherein, the vertical coordinate shows the amount of 3-5 subordinate microvessels in the area within 2.5 mm around the filter paper. "*" indicates $P<0.05$; "**" indicates $P<0.01$.

The results shown in FIGS. 2 and 3 indicated that, compared with the negative control group PBS, ZY1-4 small peptides significantly inhibited the angiogenesis in chick embryo chorioallantoic membrane both at low concentration (2 µg/µl) and high concentration (10

Example 4

Inhibition Effect of ZY1 Small Peptide on Pathological Angiogenesis in the Mouse Cornea Model of the corneal stroma micropocket was used and the methods were as follows:

Male C57BL/6 mice (aged 4-5 weeks) were intraperitoneally injected with 2% pentobarbital (about 0.1 ml/PCS) for anesthesia. 4% hydrochloric oxybuprocaine ophthalmic solution was locally administrated. Under the stereo microscope, OT syringe needle and 2 ml syringe needle was used to perform a blunt dissection between the layers of corneal stroma at 0.8-1 mm from corneoscleral limbus. A pouch of about 0.6×0.8 mm was formed. Slow-release tablets (mixture of 1:1 (v/v) of 12% poly Hydroxyethyl methacrylate (poly-HEMA): sucralfate) were planted respectively into the micropocket, including negative control group (blank tablet), positive control group (VEGF group: 320 ng/µl, 160 ng/tablet), and treatment group (VEGF+ZY1 small peptides of 1 µg/tablet low concentration, 5 µg/tablet moderate concentration, or 10 µg/tablet high concentration). 5 days after operation, the length of the longest new vessel (VL is the length of the longest new blood vessel grown from limbus to the cornea), and the clock hours of corneal neovascularization (CN represents the accumulative clock hours of corneal neovascularization) were observed. Neovascularization area were calculated as followed: Area (mm$^2$)=0.5*3.14*VL (mm)*CN*0.4 (mm). SPSS1L0.1 was used for statistical analysis.

Figure 4A:
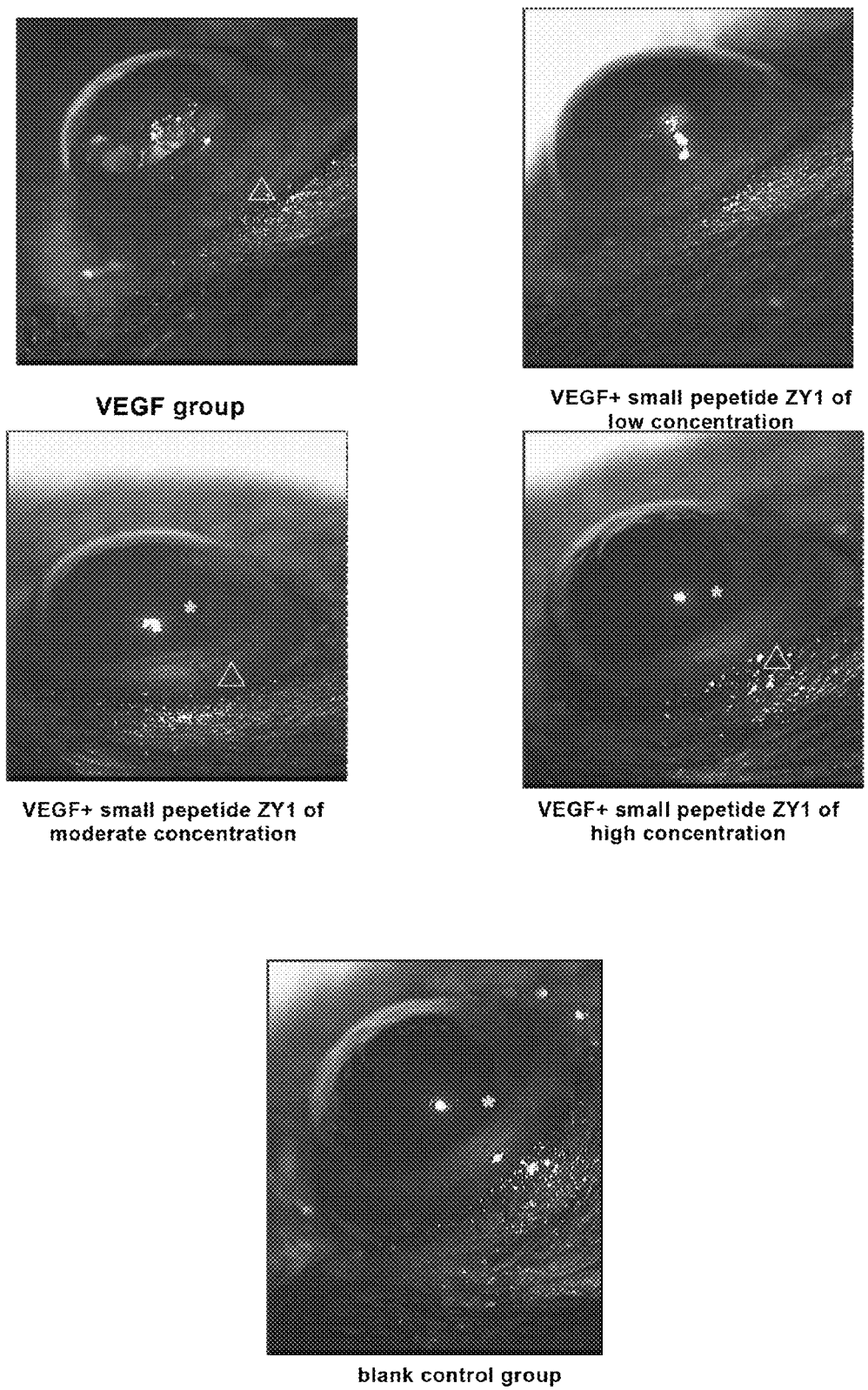
FIG. 4A shows the effect of ZY1 small peptide on the pathological angiogenesis in mouse corneal. ZY1 small peptide has a significant effect of inhibiting angiogenesis. Wherein, "*" indicates the location of the particles, "Δ" indicates the neovascularization site.
Figure 4B:
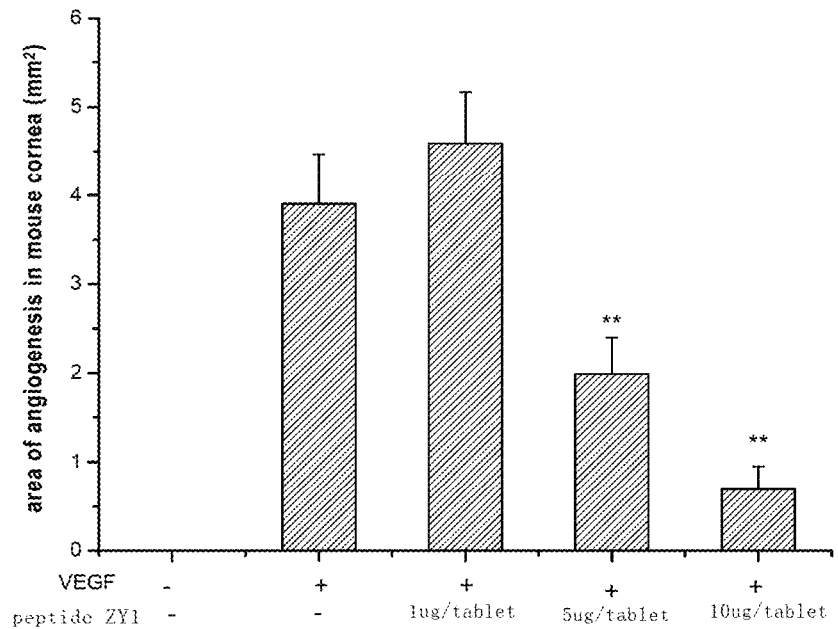
In FIG. 4B, abscissa shows: 1: blank control group (negative control group); 2: VEGF group (positive control group); 3: VEGF+low concentration (1 μg/tablet) group of ZY1 small peptide; 4: VEGF+moderate concentration (5 μg/tablet) group of ZY1 small peptide; 5: VEGF+high concentration (10 μg/tablet) group of ZY1 small peptide; the vertical coordinate shows the area of the pathological angiogenesis in mouse ($mm^2$). "**" indicates $P<0.01$.

The results shown in FIG. 4 indicated that compared with the VEGF group, ZY1 small peptides significantly inhibited the corneal angiogenesis in moderate concentration (5 µg/tablet) and high concentration (10 µg/tablet).

Example 5

Inhibition Effect of ZY1 Small Peptide on Pathological Angiogenesis in the Mouse Retina Model of retinal angiogenesis in hypoxia-induced mice was used and the methods were as follows:

Seven days after birth, C57BL/6 mice were placed together with their breast feeding mother into an environment having a 75%±2% oxygen concentration. The mice were taken out 5 days later, and were injected intravitreally with 0.50 ZY1 small peptides of low concentration (500 ng/µl), moderate concentration (1 µg/µl), high concentration (2 µg/µl) or control sample PBS. Mice were placed in an environment having normal air for further feeding, thereby forming the mice model of retinopathy induced by hypoxia. The eyeballs were removed 5 days later, fixed in 4% paraformaldehyde, embedded in paraffin, cut into sections, and stained with HE. The amount of the nucleus of the vascular endothelial cells in retina was counted under the optical microscope (Magnification was 200 fold). SPSS11.0.1 was used for statistical analysis.

Figure 5:
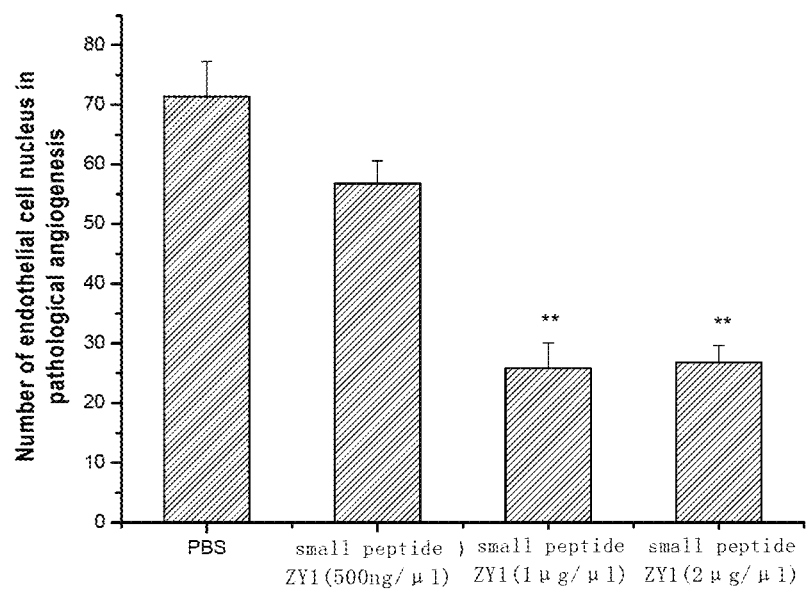
FIG. 5 shows the effect of ZY1 peptides on pathological angiogenesis in mouse retina. ZY1 small peptide has a significant effect of inhibiting angiogenesis. Wherein, abscissa shows: 1: blank control group of PBS (negative control group); 2: low concentration (500 ng/μl) group of ZY1 small peptide; 3: VEGF+moderate concentration (1 μg/μl) group of ZY1 small peptide; 4: VEGF+high concentration (2 μg/μl) group of ZY1 small peptide. The vertical coordinate shows the amount of endothelial cell nucleus of pathological angiogenesis in mouse. "**" indicates $P<0.01$.

The results shown in FIG. 5 indicated that ZY1 small peptide significantly inhibited pathological angiogenesis in mouse retina at moderate concentration (1 µg/µl) and high concentration (2 µg/µl). P<0.01, statistically significant.

Example 6

Effect of ZY1 Small Peptides on Proliferation of Primary HUVECs

The MTS method was used as follows:

Human Umbilical Vein Endothelial Cells (HUVECs) (purchased from ScienCell Co.) were inoculated onto a 96-well plate with an inoculation concentration of 4×10$^4$/ml. After cells had adhered to the wall, serum-free culture medium of ECM were added and the cells were cultivated at 37° C. for 24 hours. Then the serum-free culture medium ECM was added into each well in negative control group. VEGF (10 ng/ml) (purchased from Sigma Co.) in positive control group, VEGF (10 ng/well) ZY1 small peptide having different concentrations (1 µg/µl, 10 µg/µl, 25 µg/µl, 50 µg/µl) in treatment group were added as well. After 24 hours incubation, 20 µl MTS solution (purchased from Promega Corporation) was added in each well. After incubation at 37° C. for 4 hours, the absorbance at 490 nm for each well was measured by using Enzyme-linked Immunoassay Analysis (Bio-Rad Co.). The proliferation activity of cells was determined according to OD490. Finally, SPSS11.0.1 was used for statistical analysis.

Figure 6:
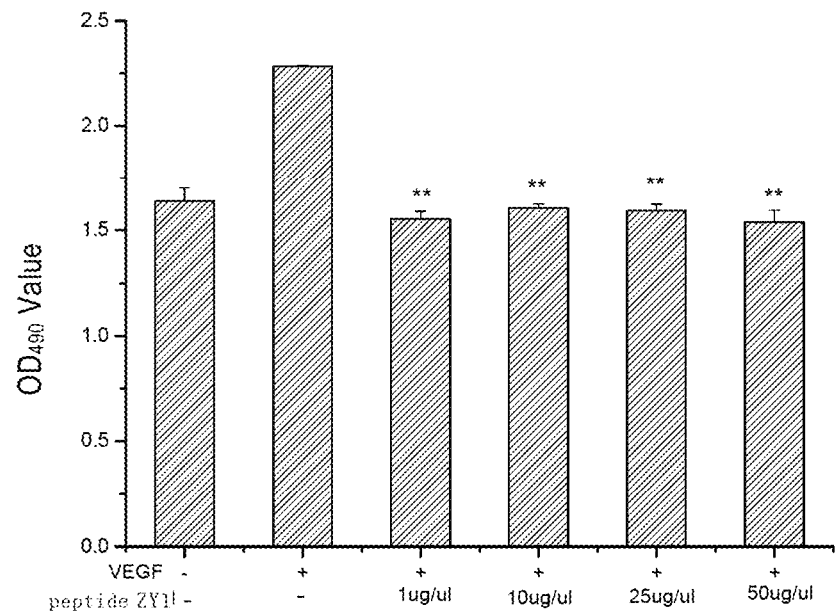
FIG. 6 shows the effect of ZY1 small peptide on proliferation of Human Umbilical Vein Endothelial Cells (HUVECs). ZY1 small peptide has a significant effect of inhibiting the proliferation of endothelial cells. Wherein, abscissa shows: 1: serum-free medium group (negative control group); 2: VEGF group (positive control group); 3: VEGF+ZY1 small peptide (1 μg/μl) group; 4: VEGF+ZY1 small peptide (10 μg/μl) group; 5: VEGF+ZY1 peptide (25 μg/μl) group; 6: VEGF+ZY1 peptide (50 μg/μl) group. The vertical coordinate shows the OD450 value of HUVECs. "*" indicates $P<0.01$.

The results shown in FIG. 6 indicated that ZY1 small peptide significantly inhibited the proliferation of HUVECs even at low concentration (1 µg/µl).

Example 7

Effect of ZY1 Small Peptide on Migration of Primary HUVECs

The Wound Healing method was used as follows:

Primary Human Umbilical Vein Endothelial Cells (HUVECs) (purchased from ScienCell Co.) were inoculated onto a 12-well plate with an inoculation concentration of 1×10$^5$/ml. After cells had adhered to the wall and grown to 80%-90% of confluence, serum-free culture medium of ECM were added before cultivation at 37° C. for 24 hours. A "+" scratch was carved with the tip of a 200 µl pipettor in each well and serum-free culture medium ECM were added in negative control group. VEGF (10 ng/ml) (purchased from Sigma Co.) in positive control group, and VEGF (10 ng/ml)+ZY1 small peptide having different concentrations (1 µg/µl, 10 µg/µl, 25 µg/µl, 50 µg/µl) in treatment group were added as well. The cultivation was continued. Photos were taken for the scratches of the cells in the 12-well plate at 0 hour and 6 hour, respectively. The average width of the scratches was calculated. The migration activity was determined according to the scratch width. Finally, SPSS11.0.1 was used for statistical analysis.

Figure 7:
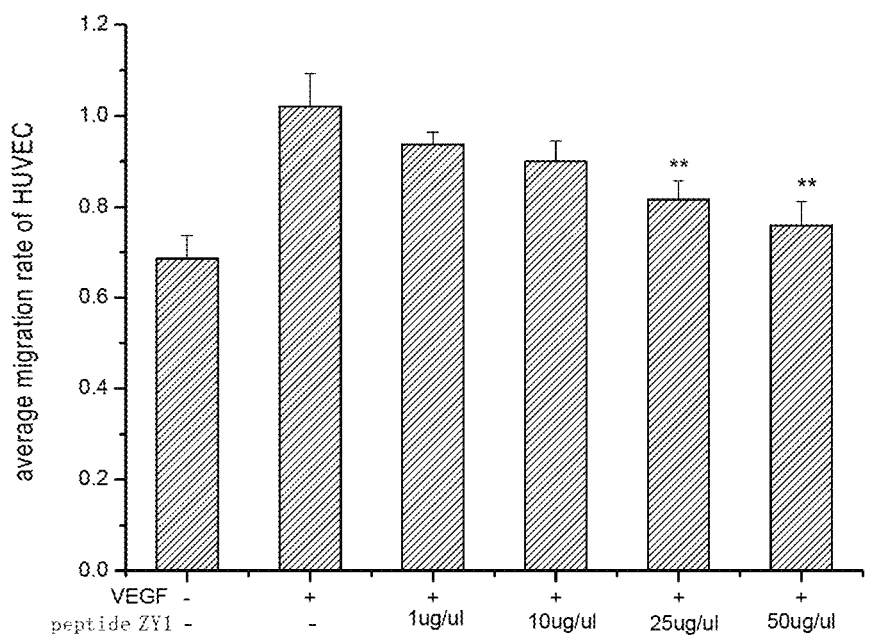
FIG. 7 shows the effect of ZY1 small peptide on migration of Human Umbilical Vein Endothelial Cells (HUVECs). ZY1 small peptide has a significant effect of inhibiting the migration of endothelial cells. Wherein, abscissa shows: 1: serum-free medium group (negative control group); 2: VEGF group (positive control group); 3: VEGF+ZY1 small peptide (1 μg/uμl) group; 4: VEGF+ZY1 small peptide (10 μg/uμl) group; 5: VEGF+ZY1 peptide (25 μg/μl) group; 6: VEGF+ZY1 peptide (50 m/μl) group. The vertical coordinate shows the average migration rate of HUVECs. "**" indicates $P<0.01$.

The results shown in FIG. 7 indicated that after treating with ZY1 small peptide for 6 hours, the migration of Primary HUVECs was significantly inhibited.

Example 8

Effect of ZY1 Small Peptide on Chemotaxis of Primary HUVECs

The Transwell Chamber method was used as follows:

HUVECs (purchased from ScienCell Co.) were inoculated onto the upper chamber of Transwell chambers with an inoculation concentration of $6 \times 10^5$/ml. Serum-free culture medium of ECM or ZY1 small peptide having different concentrations (10 µg/µl, 25 µg/µl, 50 µg/µl) were added into individual upper chambers. VEGF (50 ng/ml) (purchased from Sigma Co.) was added/not added into the lower chamber as a chemotactic factor. After incubation at 37° C. for 24 hours, the cells on upper surface of Transwell Chamber membrane were wiped and the membrane was washed with PBS. Then the membrane was fixed in 4% paraformaldehyde solution and the lower surface of membrane was stained with hematoxylin, cut and then sections were prepared. Five fields on the chamber membrane under the optical microscope (Magnification was 400 fold) were randomly taken for photograph and the number of cells nucleus was counted. The chemotaxis was determined according to the number of cells nucleus on the lower surface of chamber membrane. Finally, SPSS11.0.1 was used for statistical analysis.

Figure 8:
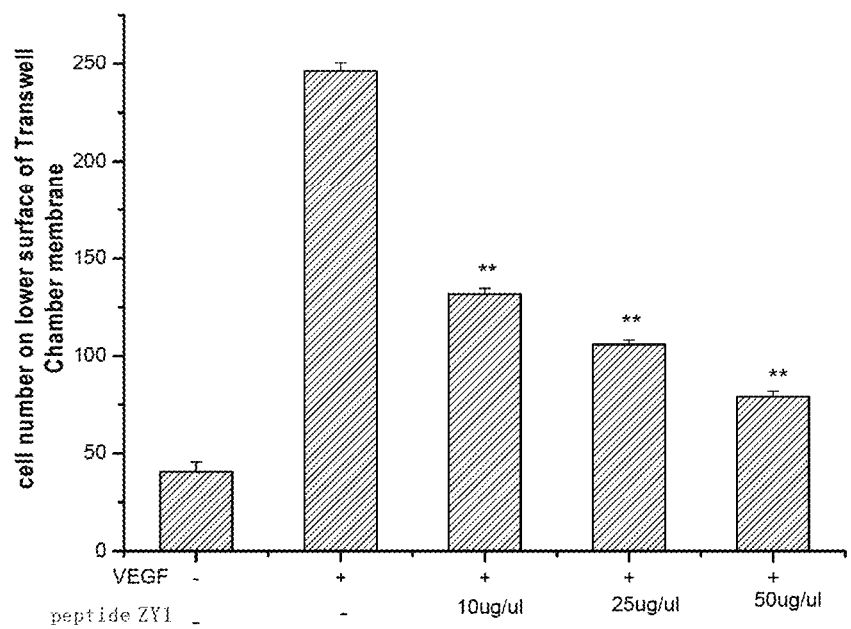
FIG. 8 shows the effect of ZY1 small peptide on chemotaxis of Human Umbilical Vein Endothelial Cells (HUVECs). ZY1 small peptide has a significant effect of inhibiting the chemotaxis of endothelial cells. Wherein, abscissa shows: 1: serum-free medium group (negative control group); 2: VEGF group (positive control group); 3: VEGF+ZY1 small peptide (10 μg/μl) group; 4: VEGF+ZY1 small peptide (25 μg/μl) group; 5: VEGF+ZY1 peptide (50 μg/μl) group. The vertical coordinate shows the amount of endothelial cells nucleus on the lower surface of Transwell Chamber membrane. "**" indicates P<0.01.

The results shown in FIG. 8 indicated that ZY1 small peptide exhibited a significant inhibition effect on chemotaxis of HUVECs.

Example 9

Effect of ZY1 Small Peptide on Lumen Formation of Primary HUVECs

The Matrigel method was used as follows:

A 50 µl/well Matrigel (purchased from BD Co.) was added into a 96-well plate before incubation at 37° C. for 30 min. After solidified, the primary HUVECs were inoculated onto the surface of the Matrigel with an inoculation concentration of $8 \times 10^6$/ml. Serum-free culture medium of ECM in negative control group, VEGF (50 ng/ml) (purchased from Sigma Co.) in positive control group, and ZY1 small peptide having different concentrations (1 µg/µl, 10 µg/µl, 25 µg/µl, 50 µg/µl) in treatment group were added into the wells. The incubation was continued at 37° C. Photos were taken for the 3 randomized fields of cells in the plate under the microscope (Magnification was 200 fold.) after 6 hours of treatment and the number of formed lumina was counted. Finally, SPSS11.0.1 was used for statistical analysis.

Figure 9:
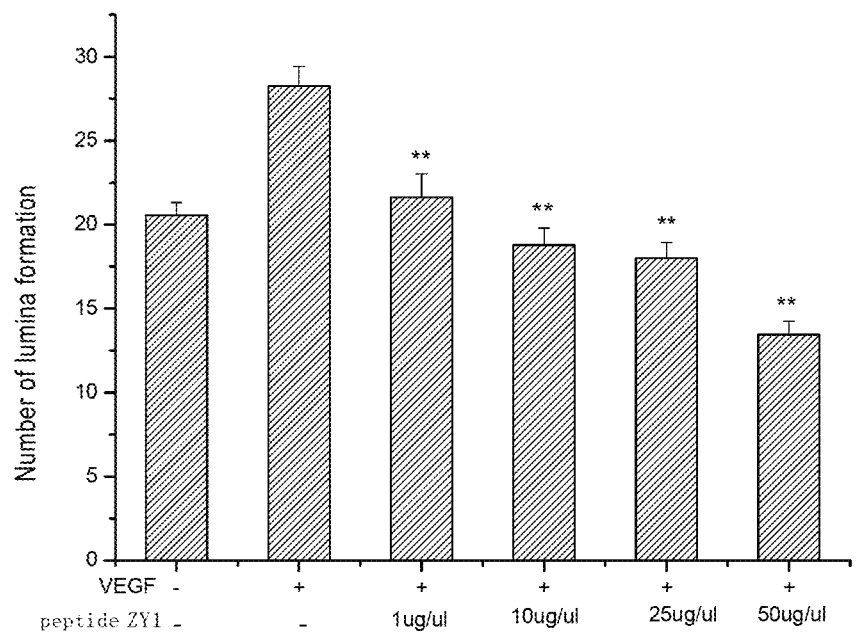
FIG. 9 shows the effect of ZY1 small peptide on lumen formation of Human Umbilical Vein Endothelial Cells (HUVECs). ZY1 small peptide has a significant effect of inhibiting the lumen formation of endothelial cells. Wherein, abscissa shows: 1: serum-free medium group (negative control group); 2: VEGF group (positive control group); 3: VEGF+ZY1 small peptide (1 μg/uμl) group; 4: VEGF+ZY1 small peptide (10 μg/μl) group; 5: VEGF+ZY1 small peptide (25μ/μl) group; 6: VEGF+ZY1 peptide (50 μg/μl) group. Ordinate shows the amount of lumina formed by HUVECs. "**" indicates: P<0.01.

The results shown in FIG. 9 indicated that ZY1 small peptide at different concentration exhibited a significant inhibition effect on the lumen formation of primary HUVECs after 6 hours of treatment.

Example 10

Preparation of Eyedrop

The following components were mixed via the conventional techniques to obtain a 1% eyedrop, the formulation of which was as follows:

| | |
|---|---|
| ZY peptide (ZY1) | 10 mg |
| Hydroxylpropyl methyl cellulose | 0.03 g |
| Sterile water | q.s. to 10 ml |

The osmotic pressure was adjusted to 300 Osm, and the pH was adjusted to 6.8-7.1.

Five volunteers used the eyedrop for one week, three times per day, and 1 drop/eye for each time. The results showed that the eyedrop could inhibit ocular angiogenesis.

Example 11

Preparation and Activity of Derived Polypeptides

Derived Polypeptides were prepared as follows, and the inhibition effect on proliferation of Human Umbilical Vein Endothelial Cells HUVECs was determined according to the methods in Example 6.

Derived Polypeptide 1: the sequence was the same as SEQ ID NO.: 1 except that Leu in position 5 was substituted by Ile.

Derived Polypeptide 2: the sequence was the same as SEQ ID NO.: 2 except that Val in position 20 was substituted by Ala.

Derived Polypeptide 3: the sequence was the same as SEQ ID NO.: 1 except that Asn in position 15 was substituted by Gln.

Derived Polypeptide 4: the sequence was the same as SEQ ID NO.: 3 except that Ala in position 2 was substituted by Val.

Derived Polypeptide 5: the sequence was the same as SEQ ID NO.: 3 except that Cys in position 1 was deleted.

The results indicated that in the treatment group of the above derived polypeptides 1-5, the proliferation of HUVEC was significantly inhibited.

Discussion

Placenta Growth Factor (PlGF) is a member of VEGF family. It was firstly isolated and purified from human placenta cDNA library by Maglinone et al. in 1991. PLGF can be detected in heart, lung, thyroid, and skeletal muscle as well as in human placenta. According to the alternative splicing of PlGF gene, 4 different isomers can be formed: PlGF-1 (PlGF131), PlGF-2(PlGF152), PlGF-3(PlGF203), and PlGF-4(PlGF224). They have different size, secretion characteristics and affinity to receptors. Two PlGF monomers form a secretory homodimer glycoprotein, which binds onto its receptors, thereby mediating the signal transduction and playing its biological roles.

In addition, PlGF can combine with VEGF to form a heterodimer, thereby influencing the signal transduction pathway of VEGF. PlGF can promote the proliferation of endothelial cells of vessels (especially microvessels), and it can regulate the growth of endothelial cells and stimulate angiogenesis as chemokines of endothelial cell growth factors. PlGF also facilitates the migration of monocytes and endothelial cells, and improve the permeability of endothelial cells. Although VEGF can also induce angiogenesis, angiogenesis induced by PlGF exhibits normal physiological characteristics instead of other abnormal changes. Such angiogenesis will not lead to edema, hemangioma, and increased permeability and so on which usually resulted from the angiogenesis induced with VEGF.

ZY1-4 small peptides of the present invention and derived polypeptide thereof were all derived from Placenta Growth Factor. The experiments have shown that the purified ZY1-4 small peptides exhibit good effect on angiogenesis inhibition in chick embryo chorioallantoic membrane. For example, ZY1 small peptide further exhibit an inhibiting effect on pathological angiogenesis in the mouse cornea, in the mouse retina, and on proliferation, migration and chemotaxis of endothelial cells in vitro. Therefore, the peptides of invention have a potential and broad application.

All references mentioned in the present invention are incorporated herein by reference, as each of them is individually cited herein by reference. Further, it should be understood that, after reading the above contents, the skilled person can make various modifications or amendments to the present invention. All these equivalents also fall into the scope defined by the pending claims of the subject application.

What is claimed is:

1. A pharmaceutical composition, comprising:
   (a) a polypeptide as set forth by the following formula I, or a pharmaceutically acceptable salt thereof,

[Xaa0]-[Xaa1]-[Xaa2]-[Xaa3]-[Xaa4]-[Xaa5]-[Xaa6]-
   [Xaa7]-[Xaa8]-[Xaa9]-[Xaa10]-[Xaa11]-
   [Xaa12]-[Xaa13]-[Xaa14]-[Xaa15]-[Xaa16]-
   [Xaa17]-[Xaa18]       (I)

wherein,
   Xaa0 is Cys;
   Xaa1 is selected from the group consisting of Val or Leu;
   Xaa2 is selected from the group consisting of Ser or Thr;
   Xaa3 is selected from the group consisting of Leu, or Ile;
   Xaa4 is selected from the group consisting of Leu, or Ile;
   Xaa5 is selected from the group consisting of Arg or Lys;
   Xaa6 is selected from the group consisting of Cys;
   Xaa7 is selected from the group consisting of Thr or Ser;
   Xaa8 is selected from the group consisting of Gly or Ala;
   Xaa9 is selected from the group consisting of Cys;
   Xaa10 is selected from the group consisting of Cys;
   Xaa11 is selected from the group consisting of Gly or Ala;
   Xaa12 is selected from the group consisting of Asp or Glu;
   Xaa13 is selected from the group consisting of Glu or Asp;
   Xaa14 is selected from the group consisting of Asn or Gln;
   Xaa15 is selected from the group consisting of Leu or Ile;
   Xaa16 is selected from the group consisting of His or Arg;
   Xaa17 is selected from the group consisting of Cys;
   Xaa18 is none, or a peptide segment consisting of 1-3 amino acids, wherein the peptide segment is one of (1) Ala, (2) Val, (3) AlaVal, (4) ValPro, (5) ValProVal, (6) AlaProAla, and (7) ValProAla;
   and the polypeptide exhibits an activity of inhibiting angiogenesis and has a length of 18-21 amino acids; and
   (b) a pharmaceutically acceptable carrier or excipient,
   wherein the polypeptide is present in an amount effective for treating a disease associated with angiogenesis, said disease associated with angiogenesis is selected from the group consisting of neovascular eye disease and a tumor, and
   wherein the amount is 10 μg to 100 mg.

2. The pharmaceutical composition of claim 1, wherein
   Xaa1 is Val;
   Xaa2 is Ser;
   Xaa3 is Leu;
   Xaa4 is selected from the group consisting of Leu and Ile;
   Xaa5 is Arg;
   Xaa6 is Cys;
   Xaa7 is Thr;
   Xaa8 is Gly;
   Xaa9 is Cys;
   Xaa10 is Cys;
   Xaa11 is Gly;
   Xaa12 is Asp;
   Xaa13 is Glu;
   Xaa14 is selected from the group consisting of Asn and Gln;
   Xaa15 is Leu;
   Xaa16 is His; and
   Xaa17 is Cys.

3. The pharmaceutical composition of claim 1, wherein the polypeptide is selected from the group consisting of:
   (a1) a polypeptide having the amino acid sequence CVS-LIRCTGCCGDENLHCVPV (SEQ ID NO: 6);
   (a2) a polypeptide having the amino acid sequence CVS-LLRCTGCCGDEQLHCVPV (SEQ ID NO: 8);
   (a3) a polypeptide having the amino acid sequence CVS-LLRCTGCCGDENLHCAPA (SEQ ID NO: 9).

4. The pharmaceutical composition of claim 1, wherein the polypeptide is a polypeptide having the amino acid sequence as set forth by SEQ ID NO:1 or 3.

5. The pharmaceutical composition of claim 1, wherein the pharmaceutical composition is an eyedrop, an injection solution, an ophthalmic gel or an eye ointment.

6. A method for treating a disease associated with angiogenesis in a mammal, wherein said disease associated with angiogenesis is selected from the group consisting of neovascular eye disease and a tumor, comprising the step of administering the pharmaceutical composition of claim 1 to a subject in need thereof.

7. A method for inhibiting angiogenesis in a mammal, comprising the step of administering the pharmaceutical composition of claim 1 to a subject in need thereof.

* * * * *

SEQUENCE LISTING

<160> NUMBER OF SEQ ID NOS: 10

<210> SEQ ID NO 1
<211> LENGTH: 21
<212> TYPE: PRT
<213> ORGANISM: Artificial Sequence
<220> FEATURE:
<221> NAME/KEY: misc_feature
<223> OTHER INFORMATION: angiogenesis-inhibiting peptide ZY1

<400> SEQUENCE: 1

Cys Val Ser Leu Leu Arg Cys Thr Gly Cys Cys Gly Asp Glu Asn Leu
1               5                   10                  15

His Cys Val Pro Val
            20

<210> SEQ ID NO 2
<211> LENGTH: 20
<212> TYPE: PRT
<213> ORGANISM: Artificial Sequence
<220> FEATURE:
<221> NAME/KEY: misc_feature
<223> OTHER INFORMATION: angiogenesis-inhibiting peptide ZY2

<400> SEQUENCE: 2

Val Ser Leu Leu Arg Cys Thr Gly Cys Cys Gly Asp Glu Asn Leu His
1               5                   10                  15

Cys Val Pro Val
            20

<210> SEQ ID NO 3
<211> LENGTH: 18
<212> TYPE: PRT
<213> ORGANISM: Artificial Sequence
<220> FEATURE:
<221> NAME/KEY: misc_feature
<223> OTHER INFORMATION: Angiogenesis-inhibiting peptide ZY3

<400> SEQUENCE: 3

Cys Val Ser Leu Leu Arg Cys Thr Gly Cys Cys Gly Asp Glu Asn Leu
1               5                   10                  15

His Cys

<210> SEQ ID NO 4
<211> LENGTH: 21
<212> TYPE: PRT
<213> ORGANISM: Artificial Sequence
<220> FEATURE:
<221> NAME/KEY: misc_feature
<223> OTHER INFORMATION: angiogenesis-inhibiting peptide ZY4

<400> SEQUENCE: 4

Cys Ala Ser Leu Leu Arg Cys Thr Gly Cys Cys Gly Asp Glu Asn Leu
1               5                   10                  15

His Cys Ala Pro Ala
            20

<210> SEQ ID NO 5
<211> LENGTH: 63
<212> TYPE: DNA
<213> ORGANISM: Artificial Sequence
<220> FEATURE:
<221> NAME/KEY: misc_feature
<223> OTHER INFORMATION: encoding sequence for angiogenesis-inhibiting
      peptide ZY1

<400> SEQUENCE: 5
tgtgtctccc tgctgcgctg caccggctgc tgcggcgatg agaatctgca ctgtgtgccg    60
gtg                                                                 63

<210> SEQ ID NO 6
<211> LENGTH: 21
<212> TYPE: PRT
<213> ORGANISM: Artificial Sequence
<220> FEATURE:
<223> OTHER INFORMATION: derived polypeptide of ZY1
<220> FEATURE:
<221> NAME/KEY: MISC_FEATURE
<223> OTHER INFORMATION: derived polypeptide of ZY1

<400> SEQUENCE: 6

Cys Val Ser Leu Ile Arg Cys Thr Gly Cys Cys Gly Asp Glu Asn Leu
1               5                   10                  15

His Cys Val Pro Val
            20

<210> SEQ ID NO 7
<211> LENGTH: 20
<212> TYPE: PRT
<213> ORGANISM: Artificial Sequence
<220> FEATURE:
<223> OTHER INFORMATION: derived polypeptide of ZY2
<220> FEATURE:
<221> NAME/KEY: MISC_FEATURE
<223> OTHER INFORMATION: derived polypeptide of ZY2

<400> SEQUENCE: 7

Val Ser Leu Leu Arg Cys Thr Gly Cys Cys Gly Asp Glu Asn Leu His
1               5                   10                  15

Cys Val Pro Ala
            20

<210> SEQ ID NO 8
<211> LENGTH: 21
<212> TYPE: PRT
<213> ORGANISM: Artificial Sequence
<220> FEATURE:
<223> OTHER INFORMATION: derived polypeptide of ZY1
<220> FEATURE:
<221> NAME/KEY: MISC_FEATURE
<223> OTHER INFORMATION: derived polypeptide of ZY1

<400> SEQUENCE: 8

Cys Val Ser Leu Leu Arg Cys Thr Gly Cys Cys Gly Asp Glu Gln Leu
1               5                   10                  15

His Cys Val Pro Val
            20

<210> SEQ ID NO 9
<211> LENGTH: 21
<212> TYPE: PRT
<213> ORGANISM: Artificial Sequence
<220> FEATURE:
<223> OTHER INFORMATION: derived polypeptide of ZY4
<220> FEATURE:
<221> NAME/KEY: MISC_FEATURE
<223> OTHER INFORMATION: derived polypeptide of ZY4

<400> SEQUENCE: 9

Cys Val Ser Leu Leu Arg Cys Thr Gly Cys Cys Gly Asp Glu Asn Leu
1               5                   10                  15

```
<210> SEQ ID NO 10
<211> LENGTH: 17
<212> TYPE: PRT
<213> ORGANISM: Artificial Sequence
<220> FEATURE:
<223> OTHER INFORMATION: derived polypeptide of ZY3
<220> FEATURE:
<221> NAME/KEY: MISC_FEATURE
<223> OTHER INFORMATION: derived polypeptide of ZY3

<400> SEQUENCE: 10

Val Ser Leu Leu Arg Cys Thr Gly Cys Cys Gly Asp Glu Asn Leu His
1               5                   10                  15

Cys
```